(12) United States Patent
Wyne et al.

(10) Patent No.: US 10,314,930 B1
(45) Date of Patent: Jun. 11, 2019

(54) TRASH RECEPTACLE GRANULE DISPENSER

(71) Applicants: Robert Wyne, Ocean City, MD (US); Rosemary Corbey, Ocean City, MD (US); Kevin R. Prince, Las Vegas, NV (US)

(72) Inventors: Robert Wyne, Ocean City, MD (US); Rosemary Corbey, Ocean City, MD (US); Kevin R. Prince, Las Vegas, NV (US)

(73) Assignee: Pioneer Concepts, LLC, Ocean City, MD (US)

( * ) Notice: Subject to any disclaimer, the term of this patent is extended or adjusted under 35 U.S.C. 154(b) by 245 days.

(21) Appl. No.: 15/476,964

(22) Filed: Mar. 31, 2017

(51) Int. Cl.
| | |
|---|---|
| *B65F 7/00* | (2006.01) |
| *B65D 83/06* | (2006.01) |
| *G01F 11/26* | (2006.01) |
| *A61L 9/01* | (2006.01) |
| *A61L 9/012* | (2006.01) |
| *B65D 83/04* | (2006.01) |
| *A61L 11/00* | (2006.01) |

(52) U.S. Cl.
CPC ............... *A61L 9/01* (2013.01); *A61L 9/012* (2013.01); *A61L 11/00* (2013.01); *B65D 83/0427* (2013.01); *B65D 83/06* (2013.01); *B65F 7/00* (2013.01); *G01F 11/261* (2013.01); *G01F 11/268* (2013.01); *B65F 2210/129* (2013.01)

(58) Field of Classification Search
CPC .. A47F 1/03; A47F 1/035; A61L 11/00; A61L 9/12; B65D 83/0427; B65D 83/0454; B65D 83/06; B65D 51/243; B65F 7/00; B65F 7/005; B65F 2210/129; G01F 11/261; G01F 11/268
USPC .......... 221/263–265; 222/166, 169, 170, 537
See application file for complete search history.

(56) References Cited

U.S. PATENT DOCUMENTS

| 125,860 | A | 4/1872 | Voss |
|---|---|---|---|
| 503,212 | A | 8/1893 | Macleod |
| 508,325 | A | 11/1893 | Lewus |

(Continued)

FOREIGN PATENT DOCUMENTS

| FR | 737942 | A | * | 12/1932 | ............ G01F 11/261 |
|---|---|---|---|---|---|
| GB | 158960 | A | * | 2/1921 | ............. A47G 19/34 |

(Continued)

*Primary Examiner* — Mollie Impink
(74) *Attorney, Agent, or Firm* — QuickPatents, LLC; Kevin Prince

(57) ABSTRACT

A dispenser for dispensing scented granules into a trash receptacle includes an enclosure having an open top end, a bottom end, and a peripheral wall. The enclosure is fixed against a bottom side of a lid to the trash receptacle with a riser tube traversing an aperture of the lid and an attachment ring. A portion control flange is fixed inside the enclosure proximate the bottom end thereof to segregate a predetermined portion of the scented granules when the enclosure is in a first upright orientation. A top end of the portion control flange is fixed with the peripheral wall which has a discharge aperture therethrough below the portion control flange. When the enclosure is placed in a second orientation inclined towards the discharge aperture, the segregated scented granules slide between the portion control flange and the enclosure to exist the discharge aperture into the trash receptacle.

11 Claims, 3 Drawing Sheets

(56) References Cited

U.S. PATENT DOCUMENTS

| | | | |
|---|---|---|---|
| 530,057 A | 11/1894 | salberg | |
| 577,747 A | 2/1897 | hansen | |
| 815,496 A | 3/1906 | Wangenheim | |
| 1,323,918 A | 12/1919 | Seraphine | |
| 1,397,260 A * | 11/1921 | Trottier | B65F 7/00 220/87.1 |
| 1,637,656 A * | 8/1927 | Radcliffe | B65F 7/00 220/371 |
| 2,802,590 A | 8/1957 | Tupper | |
| 3,102,661 A * | 9/1963 | Lundquist | B65F 1/16 220/327 |
| 3,840,145 A | 10/1974 | Almanza | |
| 4,235,849 A | 11/1980 | Handeland | |
| 5,065,886 A | 11/1991 | Sher | |
| 5,411,186 A * | 5/1995 | Robbins | B65D 47/0814 222/442 |
| 5,535,913 A | 7/1996 | Asbach | |
| 5,556,011 A * | 9/1996 | Jennings | B65D 83/06 141/325 |
| 7,086,569 B2 | 8/2006 | Stravitz | |
| 7,516,865 B1 | 4/2009 | Pierre | |
| 7,696,711 B2 | 4/2010 | Pollack | |
| 7,878,359 B1 | 2/2011 | Ko | |
| 8,122,522 B2 | 2/2012 | Looft | |
| 8,647,587 B2 | 2/2014 | Dunn | |
| 8,657,139 B1 * | 2/2014 | Bodine | A61L 9/12 220/730 |
| 8,690,017 B2 | 4/2014 | Dunn | |
| 8,910,821 B1 | 12/2014 | Stravitz | |
| 9,056,716 B1 | 6/2015 | Stravitz | |
| 9,346,617 B1 | 5/2016 | Griffin | |
| 9,428,335 B2 | 8/2016 | Hammond | |
| 2004/0140320 A1 | 7/2004 | Stravitz | |
| 2004/0265197 A1 | 12/2004 | Lin | |
| 2005/0150973 A1 | 7/2005 | Brown | |
| 2006/0081632 A1 | 4/2006 | Shieh | |
| 2007/0125792 A1 | 6/2007 | Pollack | |
| 2008/0087740 A1 | 4/2008 | Gusenoff | |
| 2009/0008394 A1 | 1/2009 | Colarusso | |
| 2011/0099942 A1 | 5/2011 | Dunn | |
| 2011/0099944 A1 | 5/2011 | Dunn | |
| 2011/0104022 A1 | 5/2011 | Dunn | |
| 2011/0226767 A1 * | 9/2011 | Ekchian | B65F 1/16 220/200 |
| 2011/0303664 A1 | 12/2011 | Nichols | |
| 2012/0234849 A1 | 9/2012 | Hughes | |
| 2013/0341328 A1 | 12/2013 | Schneider | |
| 2014/0027452 A1 | 1/2014 | Pan | |
| 2014/0138267 A1 | 5/2014 | Pirollet | |
| 2014/0183193 A1 | 7/2014 | Hammond | |
| 2015/0122813 A1 | 5/2015 | El-Taher | |

FOREIGN PATENT DOCUMENTS

| | | | | |
|---|---|---|---|---|
| GB | 795308 A | * | 5/1958 | G01F 11/261 |
| GB | 1227161 A | * | 4/1971 | G01F 11/261 |

* cited by examiner

TRASH RECEPTACLE GRANULE DISPENSER

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to trash receptacles, and more particularly to a scent granule dispenser for a trash receptacle.

DISCUSSION OF RELATED ART

Trash receptacles, and particularly covered trashed receptacles, are notorious for producing bad odors after use for several weeks or months. Typically it is impractical to clean such trash receptacles regularly, and as a result the bad odors seem to compound over time. Further, it is easy to forget to add scenting or cleaning agents to trash receptacles upon emptying.

Therefore, there is a need for a device that will automatically disburse a scenting agent into the trash receptacle regularly. Such a needed invention would further provide an easy means of refilling the device with the scenting agent, and would allow for the amount of scenting agent dispersed to be adjustable. Such a needed device would disperse the scenting agent upon lifting of the trash receptacle lid and thereby work automatically to reduce offensive odors within the trash receptacle. Even if the trash receptacle lid is not lifted for a long period of time, such a needed device would still act to reduce offensive odors within the trash receptacle. The present invention accomplishes these objectives.

SUMMARY OF THE INVENTION

The present invention is a dispenser for dispensing scented granules, pellets or powder into a trash receptacle that has a lid with an aperture therethrough. The dispenser includes an enclosure having an open top end, a bottom end, and at least one peripheral wall. The enclosure includes a top flange proximate the open top end thereof. The top flange is adapted for fixing against a bottom side of the lid of the trash receptacle. The top flange has an inner opening and an outer peripheral edge. The enclosure is adapted for holding the scented granules within an internal volume therein.

A riser tube is fixed with the inner opening of the top flange and traverses the aperture of the lid. The riser tube includes a mounting mechanism on an outer surface thereof.

An attachment ring is cooperative with the mounting mechanism on the outer surface of the riser tube. The attachment ring is adapted for selective engagement with the riser tube to clamp the lid between the attachment ring and the top flange of the enclosure. The mounting mechanism may include threads cooperative with internal threads of the attachment ring, for example.

A selectively removable top cover is adapted for sealing an open top end of the riser tube. The top cover may further include external threads cooperative with internal threads of the open top end of the riser tube.

A portion control flange is fixed inside the enclosure proximate the bottom end thereof. A lower end of the portion control flange, along with the bottom end of the enclosure, together are adapted to segregate a predetermined portion of the scented granules contained in the enclosure when the enclosure is in a first upright orientation. A top end of the portion control flange is fixed with the at least one peripheral wall of the enclosure, the at least one peripheral wall having a discharge aperture therethrough below the portion control flange.

As such, in use, when the enclosure is placed in a second orientation inclined towards the discharge aperture the segregated scented granules slide between the portion control flange and the enclosure to exist the discharge aperture into the trash receptacle.

In some embodiments the enclosure includes a plurality of vent apertures, whereby scent from the scented granules within the enclosure is able to further waft into the trash receptacle.

In some embodiments the bottom end of the enclosure is open and further includes a selectively removable bottom cover adapted for sealing the open bottom end of the enclosure. The bottom cover may further include internal threads cooperative with external threads of the open bottom end of the enclosure.

Such a removable bottom cover may be adapted to adjust the volume of the enclosure at the bottom end that captures the segregated scented granules, such that the amount of segregated scented granules dispersed with each tilting of the enclosure from the upright orientation to the second orientation is adjustable.

The present invention is a device that automatically disburses scented granules into the trash receptacle regularly with each lifting of the trash receptacle lid. The present device further provides an easy means of refilling the device with the scented granules, and allows for the amount of scented granules dispersed to be adjustable. Even if the trash receptacle lid is not lifted for a long period of time, the present invention still acts to reduce offensive odors within the trash receptacle. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
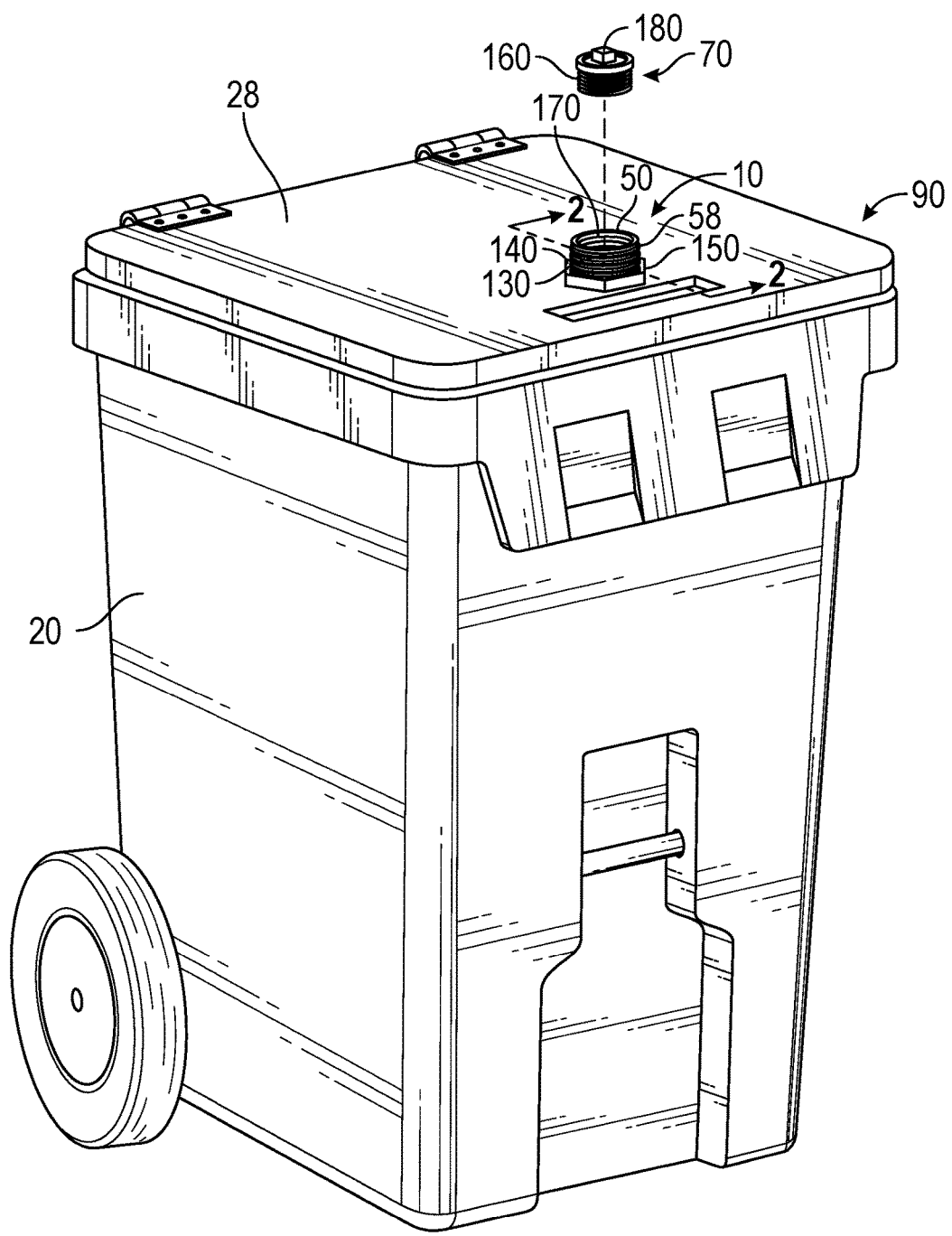
FIG. 1 is a perspective view of the invention, illustrating an enclosure thereof fixed with a trash receptacle lid and placed in a first upright orientation.
Figure 2:
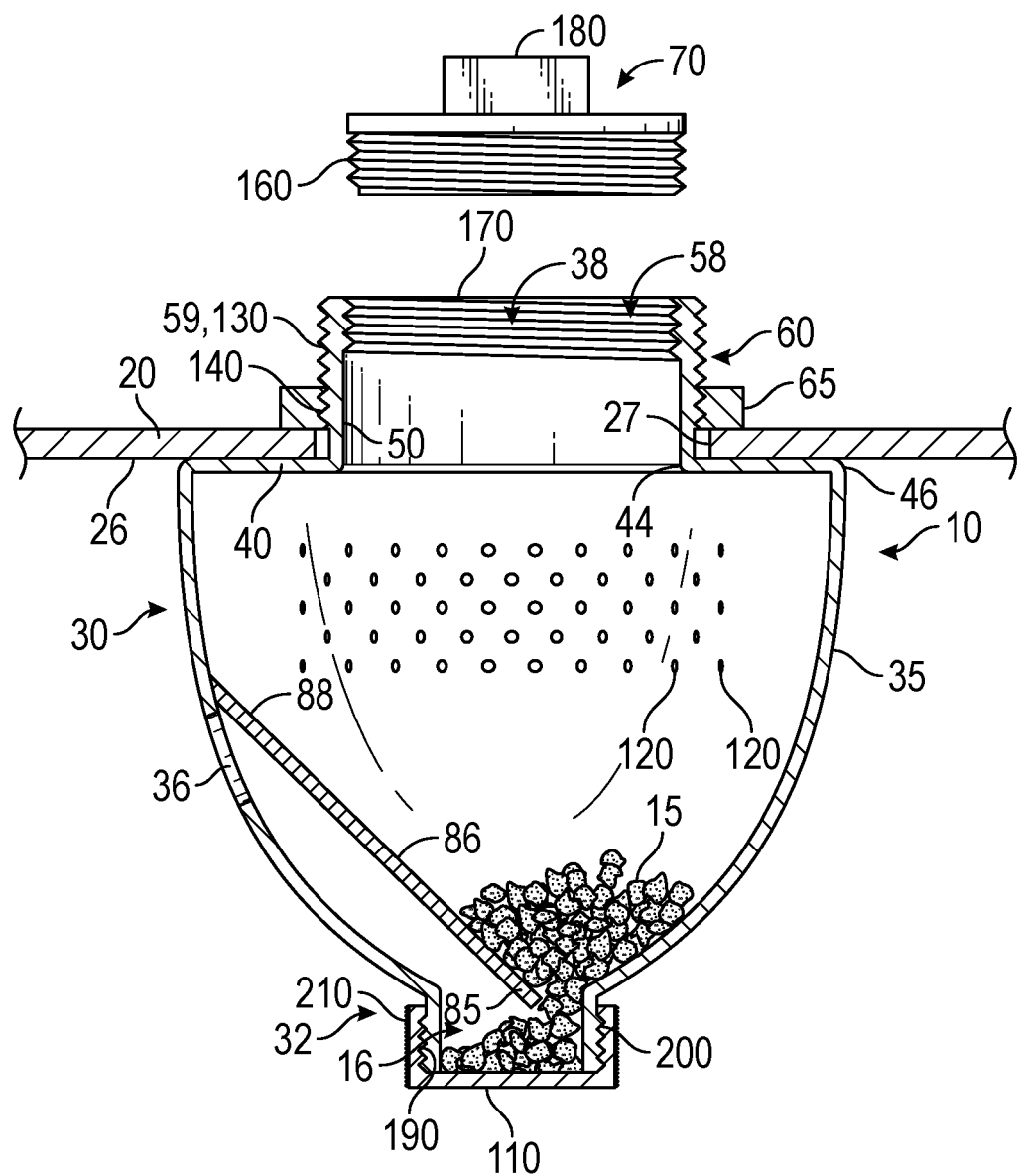
FIG. 2 is a cross-sectional view of the invention across a diameter thereof.
Figure 3:
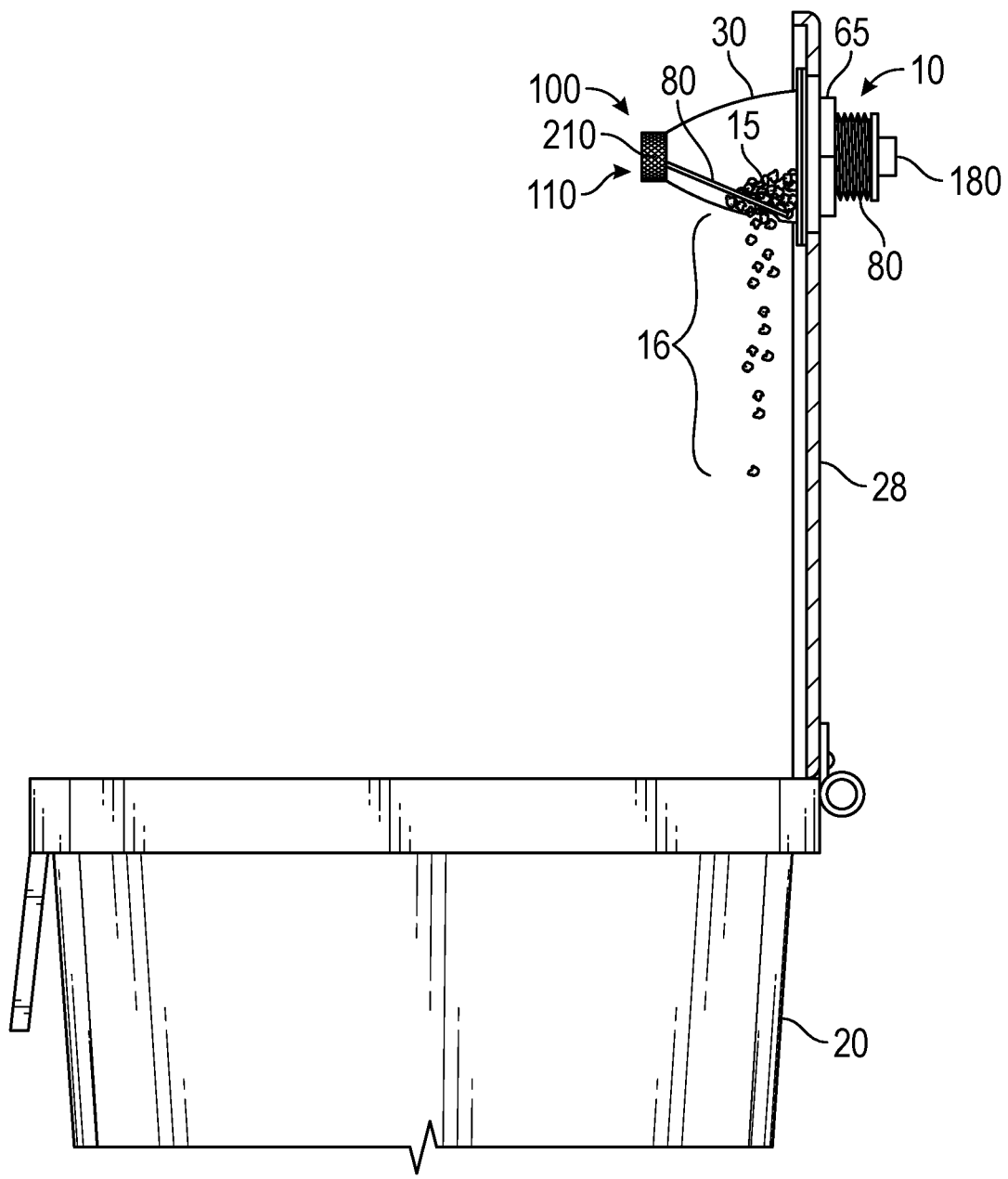
FIG. 3 is a side elevational view of the invention, illustrated with the enclosure in a second, prone position.

FIGS. 1-3 illustrate a dispenser 10 for dispensing scented granules 15 into a trash receptacle 20 that has a lid 28 with an aperture 27 therethrough. Such scented granules 15 are typically 0.1 inches to 0.25 inches in diameter, although scented pellets or powder having other granular sizes (not shown) could also be used.

The dispenser 10 includes an enclosure 30 having an open top end 38, a bottom end 32, and at least one peripheral wall 35. The enclosure 30 includes a top flange 40 proximate the open top end 38 thereof. The top flange 40 is adapted for fixing against a bottom side 26 of the lid 28 of the trash receptacle 20. The top flange 40 has an inner opening 44 and an outer peripheral edge 46. The enclosure 30 is adapted for holding the scented granules 15 therein, and is preferably made from an injection molded or roto-molded plastic material.

A riser tube 50 is fixed with the inner opening 44 of the top flange 40 and traverses the aperture 27 of the lid 28. The riser tube 50 includes a mounting mechanism 60 on an outer surface 59 thereof. Such a riser tube 50 is preferably made from a rigid plastic material.

An attachment ring 65 is cooperative with the mounting mechanism 60 on the outer surface 59 of the riser tube 50. The attachment ring 65 is adapted for selective engagement with the riser tube 50 to clamp the lid 28 between the attachment ring 65 and the top flange 40 of the enclosure 30. The mounting mechanism 60 may include threads 130 cooperative with internal threads 140 of the attachment ring 65, for example. An outer surface of the attachment ring 65 may include a wrench-engageable nut structure 150 for facilitating tightening and untightening of the dispenser 10 onto the trash receptacle lid 28. The attachment ring 65 is preferably made from a rigid plastic or metal material.

A selectively removable top cover 70 is adapted for sealing an open top end 58 of the riser tube 50. The top cover 70 may further include external threads 160 cooperative with internal threads 170 of the open top end 58 of the riser tube 50 (FIG. 2). Further, the top cover 70 may further include a second wrench-engageable nut structure 180 for facilitating tightening and untightening of the top cover 70 with the riser tube 50. The top cover 70 is preferably made from a rigid plastic or metal material.

A rigid or semi-rigid portion control flange 80 is fixed inside the enclosure 30 proximate the bottom end 32 thereof. A lower end 85 of the portion control flange 80, along with the bottom end 32 of the enclosure 30, together are adapted to segregate a predetermined portion 16 of the scented granules 15 contained in the enclosure 30 when the enclosure is in a first upright orientation 90 (FIGS. 1 and 2). A top end 88 of the portion control flange 80 is fixed with the at least one peripheral wall 35 of the enclosure 30, the at least one peripheral wall 35 having a discharge aperture 36 therethrough below the portion control flange 80. The portion control flange 80 is preferably integrally formed with the enclosure 30, but may also be adhered or ultrasonically bonded thereto.

As such, in use, when the enclosure 30 is placed in a second orientation 100 (FIG. 3) inclined towards the discharge aperture 36 the segregated scented granules 16 slide between the portion control flange 80 and the enclosure 30 to exist the discharge aperture 36 into the trash receptacle 20. Typically the trash receptacle 20 is of the typing having the lid 28 pivotally attached thereto, and as such the dispenser 10 is installed with the discharge aperture 36 oriented towards the pivoted edge of the lid 28. With trash receptacles 20 having detached lids 28, the lid 28 when removed can be pivoted manually towards the discharge aperture 36. An indicia (not shown) may be included on the enclosure 30 or lid 28 to facilitating pivoting of the lid 28 in the correct direction in order to discharge the segregated scented granules 16.

In some embodiments the enclosure 30 includes a plurality of vent apertures 120, whereby scent from the scented granules 15 within the enclosure 30 is able to further waft into the trash receptacle 20.

In some embodiments the bottom end 32 of the enclosure 30 is open and further includes a selectively removable bottom cover 110 adapted for sealing the open bottom end 32 of the enclosure 30. The bottom cover 110 may further include internal threads 190 cooperative with external threads 200 of the open bottom end 32 of the enclosure 30 (FIG. 2). The bottom cover 110 preferably further includes a knurled peripheral edge 210 for facilitating manual tightening and untightening of the bottom cover 110 with the enclosure 30.

Such a removable bottom cover 110 may be adapted to adjust the volume of the enclosure 30 at the bottom end 32 that captures the segregated scented granules 16, such that the amount of segregated scented granules 16 dispersed with each tilting of the enclosure 30 from the upright orientation 90 to the second orientation 100 is adjustable. As such, the amount of dispersed segregated granules 16 can be adjusted higher for larger trash receptacles 20, or those needing more odor abatement, or adjusted lower for smaller trash receptacles 20 or those requiring less odor abatement, such as for recyclable items or paper trash.

To install the dispenser 10 on a pre-existing trash receptacle 20 and lid 28, if the lid 28 does not already have the aperture 27 then the aperture 27 may be cut into the lid 28. Thereafter the riser tube 50 of the enclosure 30 is inserted from the bottom side 26 of the lid 28 with the discharge aperture 36 towards the rear of the trash receptacle 20, that is, the pivoted edge of the lid 28. The attachment ring 65 is then installed from above to clamp the lid 28 between the attachment ring 65 and the top flange 40 of the enclosure.

While a particular form of the invention has been illustrated and described, it will be apparent that various modifications can be made without departing from the spirit and scope of the invention. For example, the shape of the enclosure 30 may be cylindrical, square, or of other suitable shape. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A dispenser for dispensing scented granules into a trash receptacle having a lid with an aperture therethrough, comprising:
    an enclosure having an open top end, a bottom end, and at least one peripheral wall, the enclosure including proximate the open top end a top flange adapted for fixing against a bottom side of the lid of the trash receptacle, the top flange having an inner opening and an outer peripheral edge, the enclosure adapted for holding the scented granules therein;
    a riser tube fixed with the inner opening of the top flange and for traversing the aperture of the lid, the riser tube including a mounting mechanism on an outer surface thereof;
    an attachment ring cooperative with the mounting mechanism on the outer surface of the riser tube, the attachment ring adapted for selective engagement with the riser tube to clamp the lid between the attachment ring and the top flange of the enclosure;
    a selectively removable top cover adapted for sealing an open top end of the riser tube; and
    a portion control flange fixed inside the enclosure proximate the bottom end thereof, a lower end of the portion control flange along with the bottom end of the enclosure together adapted to segregate a predetermined portion of the scented granules contained in the enclosure when the enclosure is in a first upright orientation, a top end of the portion control flange fixed with the at least one peripheral wall, the at least one peripheral wall having a discharge aperture therethrough below the portion control flange;
    whereby when the enclosure is placed in a second orientation inclined towards the discharge aperture the segregated scented granules slide between the portion control flange and the enclosure to exit the discharge aperture into the trash receptacle.

2. The dispenser of claim 1 wherein the bottom end of the enclosure is open and further includes a selectively removable bottom cover adapted for sealing the open bottom end of the enclosure.

3. The dispenser of claim 1 wherein the at least one peripheral wall includes a plurality of vent apertures therethrough.

4. The dispenser of claim 1 wherein the mounting mechanism on the outer surface of the riser includes threads cooperative with internal threads of the attachment ring.

5. The dispenser of claim 4 wherein an outer surface of the attachment ring includes a wrench-engageable nut structure for facilitating tightening and untightening of the dispenser onto the trash receptacle lid.

6. The dispenser of claim 1 wherein the top cover includes external threads cooperative with internal threads of the open top end of the riser tube.

7. The dispenser of claim 6 wherein the top cover includes a second wrench-engageable nut structure for facilitating tightening and untightening of the top cover with the riser tube.

8. The dispenser of claim 2 wherein the bottom cover includes internal threads cooperative with external threads of the open bottom end of the enclosure.

9. The dispenser of claim 8 wherein the bottom cover includes a knurled peripheral edge for facilitating manual tightening and untightening of the bottom cover with the enclosure.

10. A method of dispensing scented granules into a trash receptacle having a lid, comprising the steps:
    providing an enclosure having an open top end, a bottom end, and at least one peripheral wall, the enclosure including proximate the open top end a top flange adapted for fixing against a bottom side of the lid of the trash receptacle, the top flange having an inner opening and an outer peripheral edge, the enclosure adapted for holding the scented granules therein; a riser tube fixed with the inner opening of the top flange and including a mounting mechanism on an outer surface thereof; an attachment ring cooperative with the mounting mechanism on the outer surface of the riser tube, the attachment ring adapted for selective engagement with the riser tube; a selectively removable top cover adapted for sealing an open top end of the riser tube; and a portion control flange fixed inside the enclosure proximate the bottom end thereof and adapted with the bottom end of the enclosure to segregate a predetermined portion of the scented granules contained in the enclosure when the enclosure is in a first orientation, a top end of the portion control flange fixed with the at least one peripheral wall, the at least one peripheral wall having a discharge aperture therethrough below the portion control flange;

if the lid of the trash receptacle does not have an aperture through which the riser tube can traverse, forming such an aperture through the lid of the trash receptacle;

inserting the riser tube into the lid aperture from the bottom side of the lid with the discharge aperture of the enclosure oriented towards a rear of the trash receptacle, and clamping the lid between the top flange of the enclosure and the attachment ring when the attachment ring is fully engaged with the mounting mechanism of the riser tube;

opening the top cover, filling the enclosure with the scented granules, and then closing the top cover;

dispensing the predetermined portion of the scented granules into the trash receptacle by opening and rotating the lid of the trash receptacle.

11. The method of claim 10 further including the step:

closing the lid of the trash receptacle so that another predetermined portion of the scented granules are segregated by the portion control flange.

\* \* \* \* \*